US012564646B2

(12) United States Patent
Parrish et al.

(10) Patent No.: US 12,564,646 B2
(45) Date of Patent: Mar. 3, 2026

(54) TREATMENT OF AGE-RELATED COGNITIVE DECLINE USING GENETICALLY MODIFIED VIRAL VECTORS

(71) Applicant: BIOVIVA USA, INC., Bainbridge Island, WA (US)

(72) Inventors: Elizabeth Louise Parrish, Bainbridge Island, WA (US); Patrick Ellison Sewell, Elm Grove, LA (US); Jason R. Williams, Foley, AL (US)

(73) Assignee: BIOVIVA USA, INC., Bainbridge Island, WA (US)

( * ) Notice: Subject to any disclaimer, the term of this patent is extended or adjusted under 35 U.S.C. 154(b) by 0 days.

(21) Appl. No.: 17/841,226

(22) Filed: Jun. 15, 2022

(65) Prior Publication Data

US 2022/0401583 A1     Dec. 22, 2022

Related U.S. Application Data

(60) Provisional application No. 63/211,228, filed on Jun. 16, 2021.

(51) Int. Cl.
A61K 48/00      (2006.01)
A61P 25/00      (2006.01)
A61P 25/28      (2006.01)

(52) U.S. Cl.
CPC ............ A61K 48/005 (2013.01); A61P 25/00 (2018.01); A61P 25/28 (2018.01)

(58) Field of Classification Search
CPC .................. A61K 48/005; A61P 25/28; C12N 2750/14143; C12N 15/86
See application file for complete search history.

(56) References Cited

U.S. PATENT DOCUMENTS

| | | | | |
|---|---|---|---|---|
| 6,258,791 B1 * | 7/2001 | Braun | .................... | A61K 48/00 514/44 R |
| 2019/0030138 A1 * | 1/2019 | Rodriguez | ............. | C07K 16/40 |
| 2019/0345224 A1 * | 11/2019 | Davidsohn | ................ | A61P 3/04 |

FOREIGN PATENT DOCUMENTS

| | | |
|---|---|---|
| EP | 2402038 B1 | 5/2016 |
| WO | 2012/001170 A1 | 1/2012 |
| WO | WO-2020223475 A1 * | 11/2020 ......... A01K 67/0275 |

OTHER PUBLICATIONS

Webster Scott J., Bachstetter Adam D., Nelson Peter T., Schmitt Frederick A., Van Eldik Linda J."Using mice to model Alzheimer's dementia: an overview of the clinical disease and the preclinical behavioral changes in 10 mouse models." Frontiers in Genetics, vol. 5, 2014, p. 6 [online], (Year: 2014) [retrieved on Aug. 15, 2023]. Retrieved from the internet <URL:https://www.frontiersin.org/articles/10.3389/fgene.2014.00088> <DOI=10.3389/fgene.2014.00088> (Year: 2014).*

Aschauer, Dominik F., Sebastian Kreuz, and Simon Rumpel. "Analysis of transduction efficiency, tropism and axonal transport of AAV serotypes 1, 2, 5, 6, 8 and 9 in the mouse brain." PloS one 8.9 (2013): e76310. (Year: 2013).*

Perez, Barbara A., et al. "Management of neuroinflammatory responses to AAV-mediated gene therapies for neurodegenerative diseases." Brain sciences 10.2 (2020): 119. (Year: 2020).*

International Search Report and Written Opinion received for PCT Patent Application No. PCT/US22/33831, mailed on Sep. 14, 2022, 9 pages.

International Preliminary Report on Patentability received for PCT Patent Application No. PCT/US2022/033831, mailed on Dec. 28, 2023, 7 pages.

Anonymous: "ESGCT 27th Annual Congress In collaboration with SETGyc Barcelona, Spain Oct. 22-25, 2019 Abstracts", Human Gene Therapy, vol. 30, No. 11, 221 Pages.

European Search Report received for EP Patent Application No. 22825836.4, mailed on Apr. 14, 2025, 13 pages.

Henderson SMMSSA : "ESGCT XXV Anniversary Congress in Collaboration with the German Society for Gene Therapy Oct. 17-20, 2017 Berlin, Germany", Human Gene Therapy, vol. 28, No. 12, 125 Pages.

Whittemore et al., "Telomerase gene therapy ameliorates the effects of neurodegeneration associated to short telomeres in mice", Aging, vol. 11, May 28, 2019, pp. 2916-2948.

* cited by examiner

*Primary Examiner* — Maria G Leavitt
*Assistant Examiner* — Michael Angelo Riga
(74) *Attorney, Agent, or Firm* — Workman Nydegger

(57) ABSTRACT

Disclosed herein are methods for treating or prophylactically treating age-related cognitive decline associated with dementia by administering recombinant viral vectors designed to deliver TERT and/or KL (Klotho) genes to the patient. The TERT and/or KL genes are packaged within one or more AAV viral vectors and administered to the CNS of the patient via intranasal and/or intrathecal injection. The therapy can provide improvements in cognitive function as evidenced by improved Folstein/MMSE scores over time.

16 Claims, 3 Drawing Sheets

A

B

TREATMENT OF AGE-RELATED COGNITIVE DECLINE USING GENETICALLY MODIFIED VIRAL VECTORS

CROSS-REFERENCE TO RELATED APPLICATIONS

This application claims priority to and the benefit of U.S. Provisional Patent Application No. 63/211,228, filed Jun. 16, 2021, the entirety of which is incorporated herein by this reference.

BACKGROUND

Technical Field

This disclosure generally relates to gene therapy methods and compositions used in the same. More specifically, the present disclosure relates to methods for treating or prophylactically treating age-related cognitive decline in humans.

Related Technology

Progress in the study of genetics and cellular biology over the past three decades has greatly enhanced our ability to describe the molecular basis of many human diseases. Molecular genetic techniques have been particularly effective. These techniques have allowed the isolation of genes associated with common inherited diseases that result from a lesion in a single gene such as ornithine transcarbamylase (OTC) deficiency, cystic fibrosis, hemophilias, immunodeficiency syndromes, and others. Therefore, gene therapy, defined as the introduction of genetic material into a cell in order to either change its phenotype or genotype, has been intensely investigated over the last few decades.

For effective gene therapy of many inherited and acquired diseases, it is necessary to deliver therapeutic genes to relevant cells in vivo at high efficiency, to express the therapeutic genes for prolonged (therapeutic) periods of time, and to ensure that the transduction events do not have deleterious effects. To accomplish these criteria, a variety of vector systems have been evaluated. These systems include viral vectors such as retroviruses (including lentiviruses), adenoviruses, adeno-associated viruses, and herpes simplex viruses, and non-viral systems such as liposomes, molecular conjugates, and other particulate vectors. Although viral systems have been efficient in laboratory studies, they have seen limited success in clinical applications.

In general, gene therapy vectors can be classified as two main types—viral and non-viral. The most commonly used viral gene therapy systems are retroviral vectors and adenoviral vectors, in part for historical reasons and in part because they have been relatively straightforward to make in clinically significant quantities. Retroviral and adenoviral vectors have both been used in some instances within the clinic, and some clinical trials have also been conducted using adeno-associated viral vectors, rhabdoviruses, herpes viral vectors, and vectors based on vaccinia virus or poxviruses. These viruses have various strengths and weaknesses but are all relatively efficient at delivering genes to target tissues. Limitations include difficulties in making sufficient quantities of some vectors, inability to accurately target the gene delivery in vivo, or toxic or immunological side effects of viral gene products. However, it should be noted that even with relatively efficient viral vectors, it is not reasonable at present to expect that a gene can be delivered to every affected cell (or desired target cell).

Non-viral gene therapy systems include naked DNA, DNA formulated in liposomes, DNA formulated with poly-cation condensing agents or hybrid systems, and DNA conjugated with peptides or proteins, such as single chain antibodies, to target them to specific tissues. These systems face limitations in accomplishing a long in vivo half-life, delivery to the target cell/tissue of interest, and entry into the cytoplasm and nucleus of targeted cells with attendant expression. Although there are possible solutions to each of these issues, they have not yet been efficiently combined, and efficiency of gene transfer in vivo remains an issue at this time. Thus, for these systems also, it is not reasonable at present to expect that a gene can be delivered to every desired target cell or to otherwise provide broad effects.

In an effort to allow some kind of amplification of the gene delivery events, prior efforts have attempted stimulation of the immune system, various forms of bystander effects, spread of apoptosis, antiangiogenic effects, pro-coagulant effects, replication competent viral vectors, and other mechanisms.

While intense investigation into various forms of gene therapy continues, several significant challenges remain. In particular, while gene therapy targets and associated treatment constructs are more readily identified in cases of single-gene disorders, and even in some more complex diseases such as certain cancers, some of the most significant human conditions involve highly multifaceted biological causes and effects without an easily identifiable "catch all" defect for targeted therapy. One example of such a multifaceted condition is dementia.

Dementia is typically not considered to be a specific disease, but rather a group of related conditions characterized by age-related cognitive decline that interferes with daily thinking and social functioning. Associated symptoms include memory loss (e.g., asking the same question repeatedly), impaired judgment, impaired communication (e.g., forgetting simple words and/or other difficulties with language), disorientation (e.g., getting lost in what should be a familiar location), personality or mood changes (e.g., suddenly becoming more irritable, suspicious, or fearful), loss of initiative, difficulty completing familiar tasks, problems with abstract thinking (e.g., dealing with money), and general forgetfulness (e.g., misplacing everyday items such as keys or wallets).

While dementia is relatively common, and the likelihood of dementia increases with age, it is not a normal or biologically unavoidable part of aging. There thus remains interest in determining appropriate therapies for treating, preventing, or at least slowing the onset and progression of dementia.

Dementia is characterized by three general stages: mild, moderate, and severe. Mild cognitive impairment such as general forgetfulness affects many people as they age but does not necessarily progress to dementia. For some, this type of mild cognitive impairment progresses to mild dementia that occasionally impacts daily life, with occasional confusion, disorientation, and difficulty planning and carrying out daily tasks.

In moderate dementia, daily life becomes more challenging, and the individual may find that they need help doing simple tasks such as getting dressed or combing their hair. Moderate dementia may also be associated with sleep disturbances and significant personality changes such as becoming suspicious or agitated for no reason.

In severe dementia, symptoms may have progressed to the point that there is essentially a loss of ability to communicate. Such individuals typically require full-time care. Very simple tasks, such as sitting while holding one's head up and controlling the bladder, may be lost.

Alzheimer's disease is believed to account for most cases (60-80%) of dementia. More than 10% of people aged 65 or older have Alzheimer's, and that number rises to about 33% for people aged 85 or older. There were an estimated 4.7 million people aged 65 or older in the United States with Alzheimer's in 2010, and there are an estimated 47.5 million dementia sufferers worldwide. Alzheimer's disease is characterized by protein abnormalities that cause the formation of "plaques" between brain cells and "tangles" within the cells. As Alzheimer's progresses, the brain tissue loses nerve cells and connections, and the total brain size shrinks.

Other subtypes of dementia can involve the formation of Lewy bodies. Lewy bodies are abnormal structures in the brain involving a protein called alpha-synuclein. Parkinson's disease is also associated with the presence of Lewy bodies. Although Parkinson's disease is characterized by its own set of brain changes and movement disorders, it can also lead to dementia. Dementia can also be caused, aggravated, or accelerated by other conditions such as injury, stroke, or brain tumor. Vascular dementia (i.e., multi-infarct dementia) is associated with brain death caused by hypoxia from stroke or other neurovascular issue.

Dementia is thus characterized by a variety of potential underlying causes, complex interactions between multiple biological systems, and wide-reaching impacts and symptoms. Conventional treatments often involve attempts to delay progression using general health improvements related to nutrition, supplementation, and exercise, but there have not yet been any advanced treatments, including gene therapy treatments, shown to be effective in treating dementia. There remains an ongoing need for improved treatments capable of reducing the symptoms of dementia, slowing their progression, and/or providing prophylactic treatment that delays or prevents symptom onset.

BRIEF DESCRIPTION OF THE DRAWINGS

In order to describe the manner in which the above recited and other advantages and features of the disclosure can be obtained, a particular description of the disclosure will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which.

DETAILED DESCRIPTION

Introduction

Figure 1A:
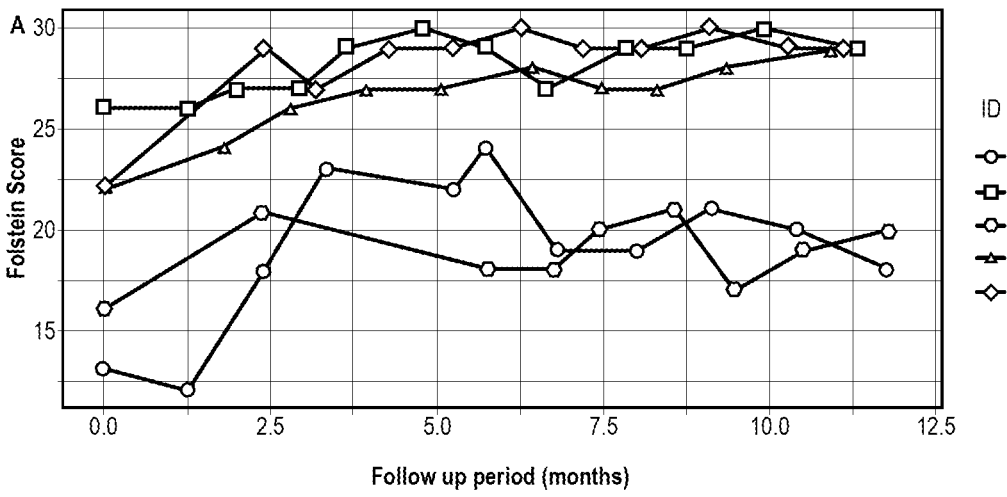
FIGS. 1A-1B illustrates Folstein/MMSE scores overtime, post-treatment, for subjects with dementia enrolled in a gene therapy treatment study in which TERT and KL genes packaged with AAV vectors were administered to the subjects via intranasal injection.

Before describing various embodiments of the present disclosure in detail, it is to be understood that any headings used herein are for organizational purposes only and are not meant to be used to limit the scope of the description or the claims. It should be further appreciated that various aspects of the present disclosure, including devices, systems, and methods, may be illustrated with reference to one or more embodiments or implementations, which are exemplary in nature. As used herein, the term "exemplary" means "serving as an example, instance, or illustration," and should not necessarily be construed as preferred or advantageous over other embodiments disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description. This disclosure is not limited to the parameters of the particularly exemplified systems, methods, apparatus, products, processes, and/or kits, which may, of course, vary. Similarly, while specific language will be used herein to describe the exemplary embodiments, it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential).

In addition, unless otherwise indicated, numbers expressing quantities, constituents, distances, or other measurements used in the specification and claims are to be understood as being modified by the term "about," as that term is defined herein. Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

It is noted that in this disclosure and particularly in the claims and/or paragraphs, terms such as "comprises," "comprised," "comprising," and the like can have the meaning attributed to it in U.S. Patent law (e.g., they can mean "includes," "included," "including," and the like); and that terms such as "consisting essentially of" and "consists essentially of" have the meaning ascribed to them in U.S. Patent law (e.g., they allow for elements not explicitly recited, but exclude elements that are found in the prior art or that affect a basic or novel characteristic of the claimed embodiments). It should, therefore, be appreciated that the terms "including," "having," "involving," "containing," "characterized by," as well as variants thereof (e.g., "includes," "has," "involves," "contains," etc.), and similar terms as used herein, including within the claims, shall be inclusive and/or open-ended, shall have the same meaning as the word "comprising" and variants thereof (e.g., "comprise" and "comprises"), and do not exclude additional un-recited elements or method steps, illustratively.

As used throughout this application the words "can" and "may" are used in a permissive sense (i.e., meaning having the potential to), rather than the mandatory sense (i.e., meaning must). Further, it will be noted that, the singular forms "a," "an," and "the"—as used in this specification and the appended claims—include plural referents unless the context clearly dictates otherwise. Thus, for example, reference to a singular referent (e.g., "widget") includes one, two, or more referents. Similarly, reference to a plurality of referents should be interpreted as comprising a single referent and/or a plurality of referents unless the content and/or context clearly dictate otherwise. For example, reference to referents in the plural form (e.g., "widgets") does not necessarily require a plurality of such referents. Instead, it will be appreciated that independent of the inferred number of referents, one or more referents are contemplated herein unless stated otherwise. The use of "or" means "and/or" unless stated otherwise. For illustration purposes, but not as a limitation, "X and/or Y" can mean "X" or "Y" or "X and Y".

All literature cited in this specification, including but not limited to, patents, patent applications, articles, books, and treatises are expressly incorporated by reference in their entirety for any purpose. In the event that any of the incorporated literature contradicts any term defined herein, this specification controls.

Embodiments of the present disclosure include recombinant viral vectors encoding a therapeutic gene, and methods of administering such vectors, for the purpose of treating or prophylactically treating age-related cognitive decline. For example, methods described herein may reduce the occurrence or severity of symptoms of age-related cognitive decline, may stop or slow the progression of symptoms, and/or may prevent the onset of symptoms. In some embodiments, a method includes administering to a patient in need thereof a therapeutically effective amount of one or more recombinant viral vectors, as explained in greater detail herein.

It should be appreciated that the disclosed treatment methods can be from the perspective of the healthcare practitioner or from the patient's perspective. For example, the exemplary embodiment above that provides for the administration of a therapeutically effective amount of one or more recombinant viral vectors to a patient in need thereof, is provided from the perspective of a healthcare provider. This same method act can alternatively be expressed from the patient's perspective—e.g., receiving a therapeutically effective amount of one or more recombinant viral vectors. The same or analogous modification can be applied to any of the recited method acts disclosed herein, unless explicitly stated otherwise, to cast a disclosed method from the perspective of a healthcare provider or from the patient/subject themselves. Throughout this disclosure, the terms "patient" and "subject" may be used interchangeably.

Dementia Assessment & Monitoring

An assessment of a patient for potential dementia typically starts with an assessment of other underlying treatable conditions such as abnormal thyroid function or nutritional deficiency. If these treatable conditions are ruled out, dementia is diagnosed, or the progression of dementia is monitored, using standard cognitive and neuropsychological tests. Two of the most commonly used standard cognitive assessments are the Mini-Mental State Exam (MMSE, also referred to as the Folstein test) and the Mini-Cog tests.

During the MMSE, a healthcare professional asks a patient a series of questions designed to test a range of everyday mental skills. The maximum MMSE score is 30 points, and scores are usually categorized such that 20-24 suggests mild dementia, 13 to 20 suggests moderate dementia, and less than 12 suggests severe dementia. For patients with Alzheimer's disease, MMSE scores decline on average about two to four points annually.

During the Mini-Cog, the patient is asked to (1) repeat the names of three common objects a few minutes after being told to remember them, and (2) draw a clock face with all 12 numbers in the correct place, and with arms showing a time specified by the healthcare professional administering the test.

Other standard cognitive assessment tests include the Medicare Annual Wellness Visit Algorithm for Assessment of Cognition (which incorporates patient history, clinician observations, and concerns expressed by the patient, family, or caregiver), the General Practitioner Assessment of Cognition (GPCOG), and the Memory Impairment Screen (MIS).

A number of other standardized tests may additionally or alternatively be used to aid in diagnosing and/or monitoring the progression of dementia. For example, the United States Food and Drug Administration (FDA) has approved several computerized cognitive tests for marketing. These include Cantab Mobile, Cognigram, Cognivue, Cognison, and Automated Neuropsychological Assessment Metrics (ANAM) devices.

Diagnosing and/or monitoring the progression of dementia can also include standard physical examination procedures, laboratory panels, depression/mood assessments, and neurological examination (to test reflexes, coordination, muscle strength, eye movement, speech, and/or sensation). Certain neurological examinations may also include brain imaging to detect and/or monitor structural brain changes.

For purposes of this disclosure, a "subject with dementia" is a subject that has suffered age-related cognitive decline such that when administered a standardized cognitive test, including any of the aforementioned tests or similar standardized tests that may be developed in the future, the resulting score is indicative of dementia. A "subject with dementia" also includes one who has received a positive diagnosis of dementia from a healthcare professional.

For purposes of this disclosure, a "subject at risk of developing dementia" includes subjects suffering from age-related cognitive decline and/or who have been indicated to be at risk of developing dementia by a healthcare professional. For example, a subject may be at risk of developing dementia if the subject suffers from cognitive decline measurable via one of the aforementioned cognitive tests (or a similar standardized test), even if the resulting scores are not yet low enough to fall within dementia categorization.

As used herein, treatment of a subject with dementia is "effective" if it is capable of one or more of: reversing one or more symptoms of dementia; reducing the occurrence or severity of one or more symptoms of dementia; slowing the progression of one or more symptoms of dementia as compared to previous or expected trends; or delaying the onset of one or more symptoms of dementia. For example, a treatment is considered effective if the rate of decline in annual MMSE scores is reduced. As mentioned above, MMSE scores for those with Alzheimer's disease decline on average about two to four points each year, and thus treatment that results in an annual decline in MMSE score less than that level (or that stops decline or improves the score) is considered "effective". As another example, a treatment is effective if the subject's progression from one stage of dementia to the next is delayed compared to the average or expected timeframe.

7                                                                                                    8

Exemplary Viral Vectors, Vector Payloads, and Compositions for Administration

As provided above, there are a number of disadvantages with current gene therapy approaches, particularly with respect to complex, multifaceted conditions such as dementia. The inventors have found that use of particular viral vectors carrying payloads of the human telomerase reverse transcriptase (TERT) gene and/or human klotho (KL) gene, when administered appropriately to the central nervous system (CNS), can beneficially treat dementia by preventing or reducing symptoms, slowing dementia progression, and/or delaying onset of additional symptoms.

The TERT gene is used to transcribe a catalytic component of the telomerase enzyme, telomerase reverse transcriptase (TERT), which plays a major role in telomerase activation. Telomeres are short-repeated DNA segments (5'-TTAGGG-3' in vertebrates) at chromosome ends, incompletely replicated during cell divisions. They protect our genetic material by acting as a chromosome cap, keeping chromosomes from binding to each other or breaking down. Once telomeres become too short, cells cease dividing and undergo apoptosis. Telomerase is responsible for adding base pairs on chromosome ends to maintain telomere length. Telomerase is highly expressed in tissues with constant and rapid cell division, such as cells in germline tissue, bone marrow, and linings in the gastrointestinal tract. In contrast, telomerase is usually undetectable or minimally active in mitotic tissues, which results in shorter telomeres with each cell division and leads to the accumulation of senescent cells. A rare autosomal dominant mutation in the gene that codes for the RNA component of telomerase causes premature aging and death, most often from infections related to bone-marrow failure. Because telomerase maintains cell proliferation and division by reducing the erosion of chromosomal ends, mice deficient in TERT, like humans with defective TERT, have shorter telomeres and a shorter life span.

Telomere shortening is observed in every individual with old age. It has been found that people 60-years of age or older that have shorter telomeres have three times the higher risk of getting heart disease, and longer telomeres are positively correlated to a longer lifespan. Despite this, there are no data to substantiate telomere length as being causative for an increased risk of heart disease or for enabling a longer lifespan. The exact mechanism and correlation of aging and telomere length remains unclear.

The KL gene encodes the klotho enzyme. Klotho is a type-I transmembrane protein within the category of β-glucuronidases and is thus capable of hydrolyzing steroid β-glucuronides. There are three subfamilies of the klotho enzyme: α-klotho, β-klotho, and γ-klotho. Unless specified otherwise, the general term "klotho" refers to the α-klotho subfamily. Known functions of klotho include control over insulin sensitivity, promoting the binding of certain fibroblast growth factors to their receptors, and modulating cellular calcium homeostasis. Klotho is also associated with suppressed oxidative stress and inflammation, particularly in endothelial tissues. Klotho is therefore believed to reduce endothelial dysfunction and atherosclerosis and to be protective of cardiac muscle cells. Klotho also plays a role in oligodendrocyte maturation and myelin integrity.

Viral vectors may include recombinant forms of lentivirus, adenoviruses, adeno-associated viruses (AAV), γ-retroviruses, cytomegalovirus, or other appropriate viral vector or plasmid thereof as known in the art. Adenovirus-associated virus-based vectors are particularly preferred for carrying the TERT and/or KL payloads described above and have been found to provide effective results. AAV can transduce both dividing and non-dividing cells with a low immune response and low toxicity. Although recombinant AAV does not integrate into the host genome, transgene expression can be long-lived.

Adenovirus-associated viruses are simple DNA containing viruses often requiring the function of other viruses (e.g., adenoviruses or herpes viruses) for complete replication efficiency. The virion is composed of a rep and cap gene flanked by two inverted terminal repeats (ITRs). These vectors can integrate into the cellular genome for stable gene transfer. However, a major hinderance to further use of these vectors has been the ability to produce them in large-scale in vitro. One obstacle to this endeavor is the toxic cellular effects of the rep and needed helper-virus genes. Examples of production methods for AAV vectors include co-transfection of plasmids delivering the ITR-flanked gene of interest with a rep-cap expression cassette and the helper-virus genes (ref); co-delivery of the ITR-flanked gene of interest along with helper-virus genes to cells stably expressing rep-cap; and/or delivery of a chimeric virus vector, such as a herpes virus vector, with all the necessary components. Another efficient method is to deliver all the required elements in a single plasmid vector.

Eleven different serotypes of AAV are currently known. Although any combination of serotypes may be utilized, preferred serotypes include AAV1, AAV2, AAV4, AAV5, AAV8, and AAV9, and particularly preferred serotypes include AAV8 and AAV9. Some embodiments may include an AAV pseudotype that mixes, for example, the capsid from one serotype with the genome from another serotype. The notation AAV8/9, for example, indicates a virus containing the genome of serotype 8 packaged in the capsid of serotype 9.

The recombinant viral vector may be designed with a variety of promoters for the incorporated TERT and/or KL genes. Suitable promoters include, for example, CAG, CBA, CBh, CAGGS, CMV early enhancer, phosphoglycerate kinase (PGK), synapsin (SYN), EF1a, EFS, ubiquitin C (UBC), or hybrids thereof. See, e.g., Haery et al. "Adeno-Associated Virus Technologies and Methods for Targeted Neuronal Manipulation" Front. Neuroanat. 26 November 2019, the entire contents of which are incorporated herein by reference. The inventors have found CMV promoters to be effective for use in TERT and/or KL applications, and such promoters are particularly preferred.

Treatment methods disclosed herein that include administration of recombinant AAV vectors carrying the TERT and/or KL genes to subjects with dementia demonstrated several beneficial effects. In particular, the MMSE scores of treated subjects showed a statistically significant improvement during the period following treatment. This is surprising given that MMSE scores are generally expected to decline by an average of two to four points a year for dementia patients. Here, treated patients not only maintained baseline scores, which by itself would have illustrated treatment effectiveness, but showed actual improvement in MMSE scores over time. Moreover, no aberrations in blood panels or brain scans were found in the treated subjects.

Compositions for in vivo administration of the vectors described herein are formulated as pharmaceutical compositions for administration to the CNS of the subject. Exemplary routes of administration include intranasal and intrathecal administration. For implementations using intranasal injection, pre-treatment of the nasal mucosa with hyaluronidase has proven to correspond to effective administration. For example, hyaluronidase may be administered to the nares and allowed to act for a period of time prior to injection of the gene therapy composition. The time period may be about 5 minutes to about 30 minutes, such as about 15 minutes, for example.

Gene therapy doses may vary according to particular application needs. Effective results have been found using a dosage on the order of about $1 \times 10^{13}$ genome copies (GC) for each type of administered vector. For example, a pharmaceutical composition may include about $0.5 \times 10^{13}$ to about $1 \times 10^{15}$ GC of a vector delivering the TERT gene, and about $0.5 \times 10^{13}$ to about $1 \times 10^{15}$ GC of a vector delivering the KL gene. More typically, a pharmaceutical composition may include about $1 \times 10^{13}$ to about $1 \times 10^{14}$ GC of a vector delivering the TERT gene, and about $1 \times 10^{13}$ to about $1 \times 10^{14}$ GC of a vector delivering the KL gene. It will be understood that these dosages are exemplary, and other implementations may utilize other dosages (higher or lower) according to particular application needs. For example, where treatment frequency is increased, there may be a concomitant decrease in dosage. On the other hand, less frequent administration may justify higher dosages. Although there is a risk of immune cascade effects at excessively high doses, certain routes of administration (e.g., systemic administration such as via intravenous injection) may justify even larger doses, such as on the order of $1 \times 10^{17}$ GC. The skilled person is capable, in light of this disclosure, of determining dosage ranges that are effective yet safe for a particular treatment regimen and route of administration.

In some embodiments, multiple vectors are utilized to deliver the same gene to the subject. For example, both a first and second vector may include the TERT gene. Additionally, or alternatively, different vectors may each include the KL gene. In some embodiments, a first vector may package the therapeutic gene (e.g., TERT and/or KL) using AAV of a first serotype and a second vector may package the same therapeutic gene using AAV of a second serotype. As a particular example shown to provide effective results, a first AAV8 vector packages TERT, and a second AAV9 vector also packages TERT. A similar AAV8 and AAV9 combination may also be utilized for delivery of KL.

In some embodiments, the TERT and KL are administered at substantially equal doses (e.g., equal number of GC of vectors designed to carry each gene). In other embodiments, TERT and KL are administered in different doses. For example, embodiments that deliver a ratio of TERT to KL of approximately 1.25 to 5, or a ratio of TERT to KL of about 1.5 to 2.5, have been found to provide effective treatment results.

Additional Recombinant Viral Vector Details

Embodiments of the present disclosure also provide a therapeutic composition comprising the recombinant virus or vector and a pharmaceutically acceptable carrier or diluent. The therapeutic composition is useful in the gene therapy and immunotherapy embodiments of the present disclosure, e.g., in a method for transferring genetic information to an animal or human in need of such, which may comprise administering to the host the composition; and embodiments of the present disclosure accordingly include methods for transferring genetic information.

In yet another embodiment, methods are provided for generating a recombinant viral vector configured to express a protein, gene product, or expression product following infection or transfection of a cell in vitro or in vivo. Within an in vitro environment, embodiments of the present disclosure provide methods for cloning or replicating a heterologous DNA sequence which may comprise infecting or transfecting a cell in vitro with a recombinant virus or vector disclosed herein and optionally extracting, purifying, or isolating the DNA from the cell or progeny virus.

Embodiments of the present disclosure provide, in another aspect, a method for preparing the recombinant viruses or vectors disclosed herein, which may comprise inserting the exogenous DNA into a non-essential region of the viral vector genome. The method can further include deleting a non-essential region from the viral genome, preferably prior to inserting the exogenous DNA.

The methods provided herein can include in vivo and/or in vitro recombination. Thus, methods of the present disclosure can include transfecting a cell with viral DNA into a cell-compatible medium in the presence of donor DNA, which may comprise the exogenous DNA flanked by DNA sequences homologous with portions of the viral genome, whereby the exogenous DNA is introduced into the viral genome, and optionally then recovering virions modified by the in vivo recombination.

The method can also include cleaving viral DNA to obtain cleaved viral DNA, ligating the exogenous DNA to the cleaved viral DNA to obtain hybrid viral-exogenous DNA, transfecting a cell with the hybrid viral-exogenous DNA, and optionally then recovering virions modified by the presence of the exogenous DNA.

Since in vivo recombination is comprehended, embodiments of the present disclosure accordingly also provide a plasmid and/or BAC system which may comprise donor DNA not naturally occurring in the viral vector encoding a polypeptide foreign to the viral vector, the donor DNA being provided within a segment of viral DNA which would otherwise be co-linear with a non-essential region of the viral genome such that DNA from a non-essential region of the virus is flanking the donor DNA.

The exogenous DNA can be inserted into the virus to generate the recombinant virus in any orientation which yields stable integration of that DNA, and expression thereof, when desired.

The exogenous DNA in the recombinant viruses or vectors described herein can include a promoter. The promoter can be from a virus, for example a herpes virus. For instance, the promoter can be a cytomegalovirus (CMV) promoter, such as a human CMV (hCMV) or murine CMV (mCMV) promoter. The promoter can also be a non-viral promoter such as the EF1a promoter. The promoter may be a truncated transcriptionally active promoter which may comprise a region transactivated with a transactivating protein provided by the virus and the minimal promoter region of the full-length promoter from which the truncated transcriptionally active promoter is derived. For purposes of this specification, a "promoter" is composed of an association of DNA sequences corresponding to the minimal promoter and upstream regulatory sequences; a "minimal promoter" is composed of the CAP site plus TATA box (minimum sequences for basic level of transcription; unregulated level of transcription); and "upstream regulatory sequences" are composed of the upstream element(s) and enhancer sequence(s). Further, the term "truncated" indicates that the full-length promoter is not completely present (i.e., that some portion of the full-length promoter has been removed), and the truncated promoter can be derived from a herpesvirus such as mCMV or hCMV (e.g., hCMV-IE or mCMV-IE). Exemplary truncated promoters can be up to a 40% and even up to a 90% reduction in size, from a full-length promoter, based upon base pairs. The promoter can also be a modified non-viral promoter.

Embodiments of the present disclosure also provide an expression cassette for insertion into a recombinant virus or plasmid which may include the truncated transcriptionally active promoter. The expression cassette can further include a functional truncated polyadenylation signal, such as an SV40 polyadenylation signal which is truncated, yet functional. Considering that nature provided a larger, longer signal, it is indeed surprising that a truncated polyadenylation signal is functional; and a truncated polyadenylation signal addresses the insert size limit problems of recombinant viruses. The expression cassette can also include exogenous or heterologous DNA with respect to the virus or system into which it is inserted, and that DNA can be exogenous or heterologous DNA as described herein. This DNA can be suitably positioned and operably linked to the promoter for expression. As to hCMV promoters, reference is made to U.S. Pat. Nos. 5,168,062 and 5,385,839, each of which is incorporated herein.

The heterologous or exogenous DNA in exemplary disclosed recombinants preferably encode an expression product, such as a therapeutic gene (e.g., TERT and/or KL, including human and/or mouse versions thereof, or other version thereof appropriate for the target subject) and/or a fusion protein (e.g., fused with a reporter, such as luciferase, or with an N- or C-terminal epitope tag, such as FLAG, 6×-His, or other epitope tag known to those having skill in the art). With respect to these terms, reference is made to the following discussion, and generally to Kendrew, THE ENCYCLOPEDIA OF MOLECULAR BIOLOGY (Blackwell Science Ltd 1995) and Sambrook, Fritsch, Maniatis, Molecular Cloning, A LABORATORY MANUAL (2d Edition, Cold Spring Harbor Laboratory Press, 1989), each of which are incorporated herein by this reference.

As to size of the DNA incorporated to form recombinant virus/vectors: the skilled artisan can maximize the size of the protein encoded by the DNA sequence to be inserted into the selected viral vector (keeping in mind the packaging limitations of the vector). To minimize the DNA inserted while maximizing or matching the native size of the protein(s) expressed, the DNA sequence(s) can exclude introns (regions of a gene that are transcribed but which are subsequently excised from the primary RNA transcript prior to translation).

With respect to expression of fusion proteins disclosed herein, reference is made to Sambrook, Fritsch, Maniatis, Molecular Cloning, A LABORATORY MANUAL (2d Edition, Cold Spring Harbor Laboratory Press, 1989) (especially Volume 3), and Kendrew, THE ENCYCLOPEDIA OF MOLECULAR BIOLOGY (Blackwell Science Ltd 1995), each of which are incorporated herein by reference. The teachings of Sambrook et al., can be suitably modified, without undue experimentation, from this disclosure, for the skilled artisan to generate recombinants expressing fusion proteins. With regard to gene therapy, reference is made to U.S. Pat. No. 5,252,479, which is incorporated herein by this reference, together with the documents cited therein and on its face.

It should be understood that the proteins and the nucleic acids encoding them may differ from the exact sequences illustrated and described herein. Thus, the invention contemplates deletions, additions, truncations, and substitutions to the sequences shown, so long as the sequences function in accordance with the methods of the invention. In this regard, substitutions will generally be conservative in nature (i.e., those substitutions that take place within a family of amino acids). For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine threonine, tyrosine. Phenylalanine, tryptophan, and tyrosine are sometimes classified as aromatic amino acids. It is reasonably predictable that an isolated replacement of a leucine with an isoleucine or valine, or vice versa; an aspartate with a glutamate or vice versa; a threonine with a serine or vice versa; or a similar conservative replacement of an amino acid with a structurally related amino acid, will typically not have a major effect on the biological activity. Proteins having substantially the same amino acid sequence as the sequences illustrated and described but possessing minor amino acid substitutions that do not substantially affect the activity or function of the protein are, therefore, within the scope of the invention.

In some embodiments, the therapeutic gene includes a recombinant nucleotide sequence. For example, in one embodiment the nucleotide sequences may be codon optimized, for example the codons may be optimized for human use. As regards codon optimization, the nucleic acid molecules of the invention have a nucleotide sequence that encodes the therapeutic proteins of the invention (i.e., telomerase and/or follistatin) and can be designed to employ codons that are used in the genes of the subject in which the protein is to be produced. Many viruses use a large number of rare codons and, by altering these codons to correspond to codons commonly used in the desired subject, enhanced expression of the recombinant genes can be achieved. In a preferred embodiment, the codons used are "humanized" codons, i.e., the codons are those that appear frequently in highly expressed human genes, (see Andre et al., J. Virol. 72:1497-1503, 1998) instead of those codons that are frequently used by or encoded by the vector/virus. Such codon usage provides for efficient expression of the transgenic viral proteins in human cells. Any suitable method of codon optimization may be used. Such methods, and the selection of such methods, are well known to those of skill in the art, and the nucleotide sequences of the inventive vectors described herein can readily be codon optimized in light of the additional teachings provided by this disclosure.

The invention further encompasses nucleotide sequences encoding functionally equivalent variants and derivatives of the viral vectors and the glycoproteins included therein. These functionally equivalent variants, derivatives, and fragments display the ability to retain functional activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions include glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the nucleotides have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the natural form of the polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877. Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448. Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877).

The various recombinant nucleotide sequences and recombinant vectors can be made using standard recombinant DNA and cloning techniques, such as those disclosed in "Molecular Cloning: A Laboratory Manual", second edition (Sambrook et al. 1989), incorporated herein by reference. However, it should generally be appreciated that the vectors used in accordance with the embodiments of the present disclosure are typically chosen such that they contain a suitable gene regulatory region, such as a promoter or enhancer, to allow for the desired level of expression of the encoded therapeutic gene. Thus, one skilled in the art can create recombinants expressing a therapeutic gene of interest and use the recombinants from this disclosure and the knowledge in the art, without undue experimentation. Moreover, from the disclosure herein and the knowledge in the art, no undue experimentation is required for the skilled artisan to construct a recombinant virus/vector that expresses a therapeutic gene of interest or for the skilled artisan to use such a recombinant virus/vector.

Embodiments of the present disclosure include a recombinant viral vector encoding one or both of the TERT and/or KL genes, or species-specific homologues thereto. For example, the TERT gene can be inserted into the viral genome with any sequence-specific motifs disclosed herein (CAP site, TATA box, non-viral promoter, etc.) such that after packaging and delivering associated virions to a patient, the recombinant TERT gene is transcribed and translated within the infected cell. Similarly, the KL gene can be inserted into the viral genome in lieu of the TERT gene. In some embodiments, however, the recombinant viral vector is engineered to incorporate both TERT and KL into each packaged virion. In one embodiment, expression of the recombinant TERT and KL genes is induced by the same promoter. Alternatively, the recombinant TERT and KL genes can be associated with separate and/or unique promoters that allow individual or separate expression of each gene.

Embodiments of the present disclosure enable various treatment methods. For example, a treatment method can include a longitudinal treatment method where a plurality of therapeutically effective dosages are provided to a patient over a period of time. In some instances, the period of time is as long as 6-12 months with dosages being administered to the patient every other month, every month, every three weeks, every other week, every week, or more regularly. In an exemplary treatment method, a therapeutically effective dosage is administered to the patient every month for 8 months. In some embodiments, the patient is a middle-aged or elderly patient. For example, the patient can be a human patient that is 50 years old, 55 years old, 60 years old, 65 years old, 70 years old, or older (or can be any age falling within a range formed by the foregoing ages). The patient can also be an animal patient having an analogously middle-age or elderly age.

Pharmaceutical Compositions

While it is possible for the compounds described herein to be administered alone, it may be preferable to formulate the compounds as pharmaceutical compositions (e.g., formulations). As such, in yet another aspect, pharmaceutical compositions useful in the methods and uses of the disclosed embodiments are provided. A pharmaceutical composition is any composition that may be administered in vitro or in vivo or both to a subject to treat, prevent, or ameliorate a condition or may otherwise be administered prophylactically to improve or maintain the health of the subject. In a preferred embodiment, a pharmaceutical composition may be administered in vivo. A subject may include one or more cells or tissues, or organisms. In some exemplary embodiments, the subject is an animal. In some embodiments, the animal is a mammal. The mammal may be a human, mouse, or primate in some embodiments. A mammal includes any mammal, such as by way of non-limiting example, cattle, pigs, sheep, goats, horses, camels, buffalo, primates, cats, dogs, rats, mice, and humans.

The compositions of the invention may be injectable suspensions, solutions, sprays, lyophilized powders, syrups, elixirs, and the like. Any suitable form of composition may be used. To prepare such a composition, a nucleic acid or vector of the invention, having the desired degree of purity, is mixed with one or more pharmaceutically acceptable carriers and/or excipients.

As used herein the terms "pharmaceutically acceptable" and "physiologically acceptable" mean a biologically compatible formulation, gaseous, liquid, or solid, or mixture thereof, which is suitable for one or more routes of administration, in vivo delivery, or contact. A formulation is compatible in that it does not destroy activity of the engineered viral vector or proteins made thereby or induce adverse side effects that outweigh any prophylactic or therapeutic effect or benefit.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH and may range from a pH of about 3 to a pH of about 11, preferably about pH 3 to about pH 7, depending on the formulation and route of administration. In alternative embodiments, it may be preferred that the pH is adjusted to a range from about pH 5 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein or may include a second recombinant vector, or second protein encoded thereby, that is useful in the treatment or prevention of aging or aging-related phenomena, as discussed herein.

Formulations, for example, for parenteral or oral administration, are most typically solids, liquid solutions, emulsions, or suspensions, while inhalable formulations for intranasal or pulmonary administration are generally liquids or powders. An exemplary pharmaceutical composition may be formulated as a lyophilized solid that is reconstituted with a physiologically compatible solvent or carrier prior to administration. Other suitable carriers or diluents can be water or a buffered saline, with or without a preservative. The recombinant vector may be lyophilized for resuspension at the time of administration or can be in solution.

Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN® PLURONICS® or polyethylene glycol (PEG).

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol, and ethanol; wetting or emulsifying agents; pH buffering substances; and the like. Liposomes are also included within the definition of pharmaceutically acceptable excipients.

For example, pharmaceutically acceptable excipients particularly suitable for use in conjunction with tablets include, for example, inert diluents, such as celluloses, calcium or sodium carbonate, lactose, calcium, or sodium phosphate; disintegrating agents, such as cross-linked povidone, maize starch, or alginic acid; binding agents, such as povidone, starch, gelatin, or acacia; and lubricating agents, such as magnesium stearate, stearic acid, or talc. Pharmaceutical compositions may also be formulated as dispersible powders and granules suitable for preparation of a suspension by the addition of suitable excipients.

As another example, pharmaceutical compositions may be formulated as suspensions comprising a recombinant vector/virus disclosed herein in admixture with at least one pharmaceutically acceptable excipient suitable for the manufacture of a suspension. Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing, or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g., dextran sulfate); glycoaminoglycans and glycosaminoglycan-like compounds (e.g., hyaluronic acid); and thickening agents, such as carbomer, beeswax, hard paraffin, or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The immunogenic compositions can be designed to introduce the viral vectors to a desired site of action and release it at an appropriate and controllable rate. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers.

Alternatively, instead of incorporating these active ingredients into polymeric particles, it is possible to entrap these materials into microcapsules. Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the viral vectors are all factors that must be considered. Examples of useful polymers are polycarbonates, polyesters, polyurethanes, polyorthoesters, and polyamides, particularly those that are biodegradable.

Microcapsules can be prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nanoparticles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition, incorporated herein by reference.

A frequent choice of a carrier for pharmaceuticals is poly (d,1-lactide-co-glycolide) (PLGA). This is a biodegradable polyester that has a long history of medical use in erodible sutures, bone plates, and other temporary prostheses where it has not exhibited any toxicity. A wide variety of pharmaceuticals, including peptides and antigens, have been formulated into PLGA microcapsules. A body of data has accumulated on the adaption of PLGA for the controlled release of compounds, for example, as reviewed by Eldridge, J. H., et al., Current Topics in Microbiology and Immunology. 1989, 146:59-66. The entrapment of compounds in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected and stabilized with one of an assortment of agents (polyvinyl alcohol (PVA), gelatin, alginates, polyvinylpyrrolidone (PVP), methyl cellulose), and the solvent removed by either drying in vacuo or by solvent extraction.

The pharmaceutical compositions may also be in the form of oil-in water emulsions. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.). The emulsion may also contain sweetening and flavoring agents. Syrups and elixirs may be formulated with sweetening agents, such as glycerol, sorbitol, or sucrose. Such formulations may also contain a demulcent, a preservative, a flavoring, or a coloring agent.

Additionally, the pharmaceutical compositions may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and an isotonic sodium chloride solution. In addition, sterile fixed oils may be employed as a solvent or suspending medium. For this purpose, any bland fixed oil may be employed including synthetic mono- or diglycerides. In addition, fatty acids such as oleic acid may be used in the preparation of injectables.

In some embodiments, cyclodextrins may be added as aqueous solubility enhancers. Preferred cyclodextrins include hydroxypropyl, hydroxyethyl, glucosyl, maltosyl and maltotriosyl derivatives of cyclodextrin. An exemplary cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al., (2002) J. Leuk. Biol. 71(3): 538-44; Ahmad-Nejad, P. et al. (2002) Eur. J. Immunol. 32(7): 1958-68; poly IC or poly AU acids, polyarginine with or without CpG (also known in the art as IC31; see Schellack, C. et al. (2003) Proceedings of the 34th Annual Meeting of the German Society of Immunology; Lingnau, K. et al. (2002) Vaccine 20(29-30): 3498-508), JuvaVax (U.S. Pat. No. 6,693,086), certain natural substances (e.g., wax D-form *Mycobacterium tuberculosis*, substances found in *Cornyebacterium parvum, Bordetella pertussis*, or members of the genus *Brucella*), flagellin (Toll-like receptor 5 ligand; see McSorley, S. J. et al. (2002) J. Immunol. 169(7): 3914-9), saponins such as Q521, Q517, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®); U.S. Pat. Nos. 4,689,338; 5,238,944; Zuber, A. K. et al. (2004) 22(13-14): 1791-8), and the CCR5 inhibitor CMPD167 (see Veazey, R. S. et al. (2003) J. Exp. Med. 198: 1551-1562). Aluminum hydroxide or phosphate(alum) are commonly used at 0.05 to 0.1% solution in phosphate buffered saline. Other adjuvants that can be used include cholera toxin, especially CTA1-DD/ISCOMs (see Mowat, A. M. et al. (2001) J. Immunol. 167(6): 3398-405); polyphosphazenes (Allcock, H. R. (1998) App. Organometallic Chem. 12(10-11): 659-666; Payne, L. G. et al. (1995) Pharm. Biotechnol. 6: 473-93); cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919); immunoregulatory proteins such as CD4OL (ADX40; see, for example, WO03/063899), and the CD1a ligand of natural killer cells (also known as CRONY or a-galactosyl ceramide; see Green, T. D. et al., (2003) J. Virol. 77(3): 2046-2055); immunostimulatory fusion proteins such as IL-2 fused to the Fc fragment of immunoglobulins (Barouch et al., Science 290:486-492, 2000); and co-stimulatory molecules B7.1 and B7.2 (Boyer)—all of which can be administered either as proteins or in the form of DNA, in the same viral vectors as those encoding the therapeutic gene(s) of the embodiments disclosed herein or on separate expression vectors.

Exemplary Dosages and Treatment Regimens

Pharmaceutical compositions disclosed herein contain a total amount of the active ingredient(s) sufficient to achieve an intended therapeutic effect. The pharmaceutical compositions may, for convenience, be prepared or provided as a unit dosage form. Preparation techniques include bringing into association the active ingredient (e.g., the recombinant virus/vectors) and pharmaceutical carrier(s) and/or excipient(s). In general, pharmaceutical compositions are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient in a free-flowing form such as a powder or granules, optionally mixed with a binder, lubricant, inert diluent, preservative, surface-active or dispersing agent. Molded tablets may be produced by molding, in a suitable apparatus, a mixture of powdered compound moistened with an inert liquid diluent. The tablets may optionally be coated or scored and may be formulated so as to provide a slow or controlled release of the active ingredient therein.

Compounds including disclosed pharmaceutical compositions can be packaged in unit dosage forms for ease of administration and uniformity of dosage. A "unit dosage form" as used herein refers to a physically discrete unit suited as unitary dosages for the subject to be treated; each unit containing a predetermined quantity of compound optionally in association with a pharmaceutical carrier (e.g., excipient, diluent, vehicle or filling agent) which, when administered in one or more doses, is calculated to produce a desired effect (e.g., prophylactic or therapeutic effect or benefit). Unit dosage forms can contain a weekly or monthly dose, or an appropriate fraction thereof, of an administered compound. Unit dosage forms also include, for example, capsules, troches, cachets, lozenges, tablets, ampules, and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. The individual unit dosage forms can be included in multi-dose kits or containers. Pharmaceutical formulations can be packaged in single or multiple unit dosage forms for ease of administration and uniformity of dosage.

The compositions disclosed herein can be administered in accordance with the methods at any frequency and as a single bolus or multiple doses, for as long as appropriate. Exemplary frequencies are typically from 1-5 times, 1-3 times, 2-times, or once monthly. Timing of contact and administration ex vivo or in vivo can be dictated by the infection or pathogenesis of the viral vector used or by the concentration of the therapeutic protein in the patient (e.g., in serum or within specified organ tissue). In some embodiments, the compounds will be administered for a period of continuous therapy, for example for a week or more, or for months or years. Long-acting pharmaceutical compositions may be administered twice a week, every 3 to 4 days, every week, or once a month depending on half-life and clearance rate of the particular formulation. For example, in an embodiment, a pharmaceutical composition contains an amount of a compound as described herein that is selected for administration to a patient once a month for 6-12 months.

Doses may vary depending upon whether the treatment is therapeutic or prophylactic, the onset, progression, severity, frequency, duration, probability of or susceptibility of the age-related symptom, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the symptom(s) or pathology, and any adverse side effects of the treatment or therapy. The skilled artisan will appreciate the factors that may influence the dosage, frequency, and timing required to provide an amount sufficient or effective for providing a prophylactic or therapeutic effect or benefit. The exact dosage will be determined by the practitioner, in light of factors related to the subject that requires treatment. Dosage and administration are adjusted to provide sufficient levels of the active agent(s) or to maintain the desired effect.

The dosage may range broadly, depending upon the desired effects and the therapeutic indication. Alternatively, dosages may be based and calculated upon the per unit weight of the patient, as understood by those of skill in the art. In instances where human dosages for compounds have been established for at least some conditions, those same dosages may be used, or dosages that are between about 0.1% and 500%, more preferably between about 25% and 250% of the established human dosage. Where no human dosage is established, as will be the case for newly discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

Dosage amount and interval may be adjusted individually to provide plasma levels of the active protein, which are sufficient to maintain the modulating effects, or minimal effective concentration (MEC) thereof. For example, therapeutic dosages of follistatin may result in plasma levels of 0.05 mg/mL, 0.1 mg/mL, 0.5 mg/mL, 1 mg/mL, 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, a range bounded by any two of the aforementioned numbers, or about any of the aforementioned numbers and ranges. As another example, therapeutic dosages of telomerase may result in plasma levels of 100 mg/mL, 150 mg/mL, 200 mg/mL, 250 mg/mL, 300 mg/mL, 350 mg/mL, 400 mg/mL, 450 mg/mL, 500 mg/mL, 550 mg/mL, 600 mg/mL, a range bounded by any two of the aforementioned numbers, or about any of the aforementioned numbers and ranges. In some embodiments, the therapeutic dose is sufficient to establish plasma levels in the range of about 250 mg/mL to about 400 mg/mL. The MEC may vary for each compound but can be estimated from in vitro or ex vivo data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration. It should be appreciated that the desired serum concentration of target protein may be adjusted or dosed according to the total number of viral genomes per kg of patient body weight required to reach the desired serum concentration.

As described herein, the methods of the embodiments also include the use of a compound or compounds as described herein together with one or more additional therapeutic agents for the treatment of aging-related disorders or conditions. Thus, for example, the combination of TERT and FS344 vectors may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially (e.g., in separate solution, emulsion, suspension, tablets, pills or capsules) or by different injections in separate syringes. In general, during alternation therapy, an effective dosage of each active ingredient is administered sequentially (e.g., serially), whereas in simultaneous therapy, effective dosages of two or more active ingredients are administered together. Various sequences of intermittent combination therapy may also be used.

As used herein, all numerical values or numerical ranges include integers within such ranges and fractions of the values or the integers within ranges unless the context clearly indicates otherwise. Thus, to illustrate, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 0-72 hrs, includes 1, 2, 3, 4, 5, 6, 7 hrs, etc., as well as 1, 2, 3, 4, 5, 6, 7 minutes, etc., and so forth. Reference to a range of doses, such as 0.1-1 μg/kg, 1-10 μg/kg, 10-25 μg/kg, 25-50 μg/kg, 50-100 μg/kg, 100-500 μg/kg, 500-1,000 μg/kg, 1-5 mg/kg, 5-10 mg/kg, 10-20 mg/kg, 20-50 mg/kg, 50-100 mg/kg, 100-250 mg/kg, 250-500 mg/kg, includes 0.11-0.9 μg/kg, 2-9 μg/kg, 11.5-24.5 μg/kg, 26-49 μg/kg, 55-90 μg/kg, 125-400 μg/kg, 750-800 μg/kg, 1.1-4.9 mg/kg, 6-9 mg/kg, 11.5-19.5 mg/kg, 21-49 mg/kg, 55-90 mg/kg, 125-200 mg/kg, 275.5-450.1 mg/kg, etc. A series of ranges, for example, 1-10 μg/kg, 10-25 μg/kg, 25-50 μg/kg, 50-100 μg/kg, 100-500 μg/kg, 500-1,000 μg/kg, 1-5 mg/kg, 5-10 mg/kg, 10-20 mg/kg, 20-50 mg/kg, 50-100 mg/kg, 100-250 mg/kg, 250-500 mg/kg, includes 1-25 μg/kg, 10-25 μg/kg, 25-100 μg/kg, 100-1,000 μg/kg, 1-10 mg/kg, 1-20 mg/kg etc.

Co-Administration

As used herein, "co-administration" means concurrently or administering one substance followed by beginning the administration of a second substance within 24 hours, 20 hours, 16 hours, 12 hours, 8 hours, 4 hours, 1 hour, 30 minutes, 15 minutes, 5 minutes, 1 minute, a range bounded by any two of the aforementioned numbers, and/or about any of the aforementioned numbers. In some embodiments, co-administration is concurrent.

Some embodiments are directed to the use of companion diagnostics to identify an appropriate treatment for the patient. A companion diagnostic is an in vitro diagnostic test or device that provides information that is highly beneficial, or in some instances essential, for the safe and effective use of a corresponding therapeutic composition. Such tests or devices can identify patients likely to be at risk for adverse reactions as a result of treatment with a particular therapeutic composition. Such tests or devices can also monitor responsiveness to treatment (or estimate responsiveness to possible treatments). Such monitoring may include schedule, dose, discontinuation, or combinations of therapeutic compositions. In some embodiments, the therapeutic gene is selected by measuring a biomarker in the patient. The term biomarker includes, but is not limited to, genetic elements (e.g., expression level of a genetic element) or proteins (e.g., increase/decrease in expression level of a protein or concentration within a specific tissue or organ).

Abbreviated List of Defined Terms

To assist in understanding the scope and content of the foregoing and forthcoming written description and appended claims, a select few terms are defined directly below.

The term "healthcare provider" as used herein generally refers to any licensed and/or trained person prescribing, administering, or overseeing the diagnosis and/or treatment of a patient or who otherwise tends to the wellness of a patient. This term may, when contextually appropriate, include any licensed medical professional, such as a physician (e.g., medical doctor, doctor of osteopathic medicine, etc.), a nurse practitioner, a nurse, a physician's assistant, a chiropractor, a veterinarian, etc. Similarly, the term "physician" as used herein generally refers to a medical doctor, such as a general practice physician, but may particularly refer to a specialized medical doctor, such as an endocrinologist, oncologist, surgeon, radiologist, or other specialized medical doctor that may be involved in the treatment or maintenance of a patient's wellness. This term may, when contextually appropriate, include any other medical professional, including any licensed medical professional or other healthcare provider, as that term is defined herein.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein, the term "patient" generally refers to any animal, for example a mammal, under the care, observation, or treatment of a healthcare provider, with particular reference to humans under the care of a primary care physician, infectious disease specialist, or other relevant medical professional that may diagnose or treat viral infections. For the purpose of the present application, a "patient" may be interchangeable with an "individual" or "subject." Accordingly, in some embodiments, the subject is a human patient. It should be appreciated, however, that a "subject" does not necessarily have to be a "patient," as that term is described herein.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature or is linked to another nucleotide sequence or found in a different arrangement in nature. It is understood that manipulated "by man" means manipulated by some artificial means, including by use of machines, codon optimization, restriction enzymes, etc.

Unless defined otherwise, all technical and scientific terms used herein have the same meaning as commonly understood by one of ordinary skill in the art to which the present disclosure pertains.

Conclusion

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatuses disclosed herein may be made without departing from the scope of the disclosure or of the invention. Thus, while various aspects and embodiments have been disclosed herein, other aspects and embodiments are contemplated. All changes that come within the meaning and range of equivalency of the claims are to be embraced within their scope.

EXAMPLES

Study Design

An efficacy study was designed as an uncontrolled interventional and non-randomized study. Such uncontrolled studies are appropriate when patients are not expected to get better on their own and the treatment is not expected to have serious side effects, conditions met by the present study. Moreover, there is a lack of real-world gene therapy conditions with which this study could be compared.

Study Participants

Five patients were enrolled. Inclusion criteria for participation in the study were: a probable dementia and/or Alzheimer's disease diagnosis based on criteria of the NIA-AA (U.S. National Institute on Aging and Alzheimer's Association) guidelines; age of 40 or older (female patients must be post-menopausal); high school graduate or higher education; and ability to comply with immunosuppression protocol. The immunosuppression protocol required daily oral dosing of an immunosuppressing drug compatible with medical history for 6-8 weeks following treatment. Default medications were cyclosporin or prednisone.

Exclusion criteria for the study included: patients with severe aphasia or physical disability who were unable to complete neurophysiological examination; patients with mental illness; patients with a history of alcoholism and drug addiction, traumatic brain injury, epilepsy, encephalitis, normal-pressure hydrocephalus, or other neurological disorders causing cognitive impairment; patients with system diseases causing dementia (e.g., liver and kidney insufficiency, endocrine disorders, vitamin deficiencies); subjects who are unwilling or unable to abide by the study requirements; significant renal or hepatic impairment; scheduled elective surgery during the study; life expectancy of less than 6 months; participation in another research study involving an investigational product in the past 12 weeks; hypersensitivity to product constructs; active viral infection based on clinical observations; immunodeficiency; serological evidence of HIV or Hepatitis A, B, or C infection; immunosuppressive therapy ongoing or within 3 months of starting the study; taking drugs for treatment of myopathy or neuropathy or taking drugs to treat diabetes mellitus; and/or history of angina or history of myocardial infarction in the past 6 months.

Pre-Treatment Assessments

A complete medical exam was completed prior to treatment. Blood panels were also obtained and measured: calcium, phosphorus, glucose, sodium, potassium, chloride, bicarbonate, blood urea nitrogen (BUN), creatinine, alanine aminotransferase (ALT), aspartate transaminase (AST), bilirubin, alkaline phosphatase, gamma glutamyl transpeptidase (GGT), lactic dehydrogenase (LDH), uric acid, albumin, globulin and sedimentation rate (per protocol schedule per visit), complete blood count (CBC), red blood cells (RBC), hemoglobin (HgB), hematocrit (HCT), mean corpuscular volume (MCV), mean corpuscular hemoglobin (MCH), mean corpuscular hemoglobin concentration (MCHC), platelets and white blood cells (WBC) with differential, neutrophils or polymorphonuclear cells (Polys), lymphocytes (lymphs), monocytes or macrophages (Monos), eosinophils (Eos), basophils (Bas), specific gravity, pH, color, protein, glucose, casts, and porphyrins and byproducts (UTI screening).

Baseline MRI brain scans (without contrast, weighted imaging) and carotid artery ultrasound screens were also obtained for each patient. Baseline MMSE scores (i.e., Folstein scores) were also obtained.

Administration Via Intranasal Injection

Witnessed informed consent was obtained from the patient/family/guardian. Each patient was placed in the supine position with the neck hyperextended. A composition of 20% benzocaine or lidocaine was administered to the right and left intranasal mucosa. Submucosal hyaluronidase was administered to both the right and left nares. A 15-minute pause was initiated, after which a hypodermic needle was used to inject the gene therapy agent into the submucosa of the right and left nares. Each patient remained in the supine reclined position for an additional 5 minutes and after confirming that the patient had no immediate undesired effects or side effects from the procedure, the patient was discharged from the operative suite and clinic in good condition. The administered gene therapy dose was $2 \times 10^{13}$ GC AAV8-CMV-hTERT, $2 \times 10^{13}$ AAV9-CMV-hTERT, and $2 \times 10^{13}$ AAV9-CMV-KL (i.e., α-klotho). Subjects then underwent the immunosuppression regimen described above. Default medications were cyclosporin or prednisone.

Statistical Analysis

Initially, a linear model was developed considering the follow up months as independent variable and Folstein test score as the dependent variable. Age and gender were included in the models to evaluate interactions with follow up time and to obtain adjusted effect sizes. Non-linear associations were assessed with generalized additive models. The follow up time showed a non-linear association with Folstein testing score and a piece-wise linear function was adopted. The know position was determined using the loglikelihood ratio test. The linear model showed a significant overdispersion (i.e., residual deviance=666.81, df=39, P<0.001).

Each followed up person had a different Folstein testing score to start with making it justifiable to include random intercepts to the model. Therefore, a mixed effect model was fitted incorporating individual level random effects. The variance of the individual level random effect was significantly different from zero (delta deviance=37.5, df=1, P<0.001). Therefore, mixed effect model with individual level random effects were considered as the final model.

Pre and post comparison were done with Wilcoxon Rank Sum test. A P value of 0.05 was considered as significant. R programming language version 3.6.3 were used in the analysis.

Post-Treatment Monitoring

Follow up cognitive testing was performed approximately every month following treatment, and Folstein/MMSE scores were recorded. Additional blood work and doctor office visits were scheduled for the 3, 6, 9, 12, and 24 month periods. Additional brain imaging was also scheduled for the months following treatment.

The five patients with mild or moderate dementia were studied for a period of 12 to 15 months (median=13.4 months, interquartile range=12.6 to 14.6 months). Three were males (68, 83 and 86 years) and two were females (83 and 84 years).

Figure 1B:
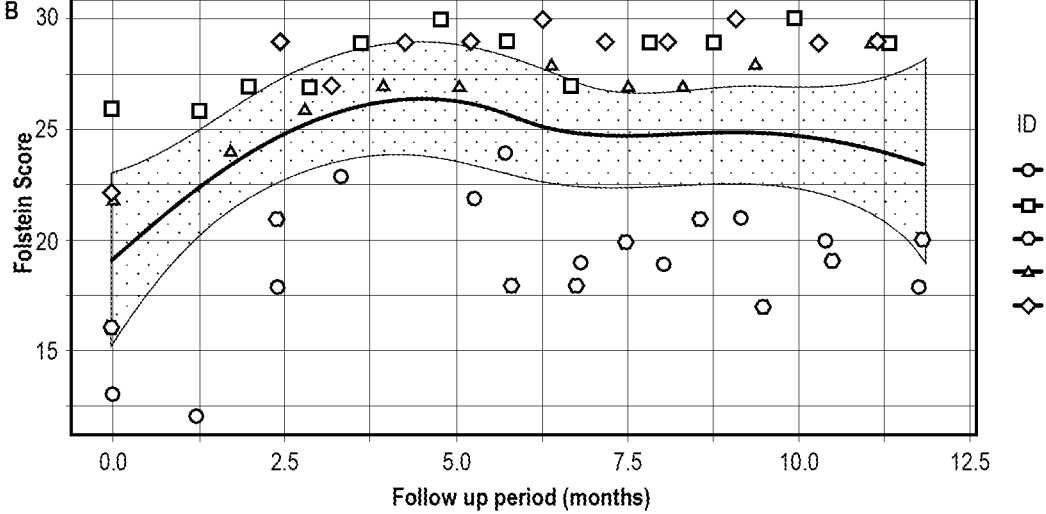

Improvements in Cognitive Function as Indicated by Improved Cognitive Test Scores Initial Folstein testing scores of the patients ranged from 13 to 26 (median=22, interquartile range=16-22). The changes in the Folstein testing scores for the follow up is shown in FIGS. 1A and 1B. There was a sharp increase in cognitive test scores during the first quarter after treatment the scoring decreased somewhat and levelled off until around 5 months. According to the fitted mixed effect linear model, the Folstein testing showed an increase from the baseline after the intervention. There was a sharp increase in cognitive test scores during the first 3.5 months after treatment with the average per month test score increase being 1.7 points. The age or gender did not show significant effect on the scoring nor interaction with the follow up time.

Cognitive assessment before treatment and serial cognitive testing after treatment demonstrated a rapid improvement in cognitive function during the first 3.5 months after which the improvement slowed until it leveled off at five months. Thereafter there is a slight decrease in slope in the average test score with an average drop of 0.07 points per month. Given that patients with dementia typically show a higher annual decline on the Folstein test, the results indicate that the AAV hTert and Klotho gene transfer therapy was successful, and the effects of that gene therapy slowed or even reversed some of the dementia pathology.

MRI Analysis

Pretreatment brain MM compared to post-treatment brain MM demonstrated no significant changes. This is not surprising considering the imaging was separated by only 10 months. With longer follow-up and continued or sustained cognitive gains, one would expect to see additional morphologic changes in the brain which might include a decreased rate of atrophy or stabilization of anatomical structures, possibly a cessation of further atrophy, and even possibly, a measurable reversal of structure atrophy. Diminishing Amyloid Beta plaque presence and reduction of Tau tangles may become evident, and Functional MM might show some slowing or reversal of the regional hypometabolism seen on Functional MRI as dementia advances.

Telomere Length & Biological Age

Figure 2A:
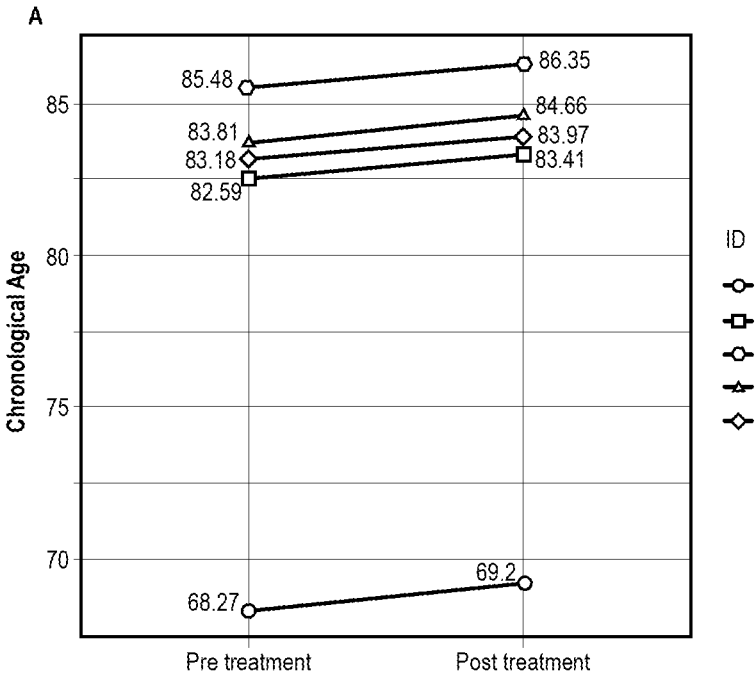
FIGS. 2A-2D illustrate pre-treatment and post-treatment values relating to chronological and biological age, median telomere length, and short telomere length ($20^{th}$ percentile) for the participating patients.
Figure 2B:
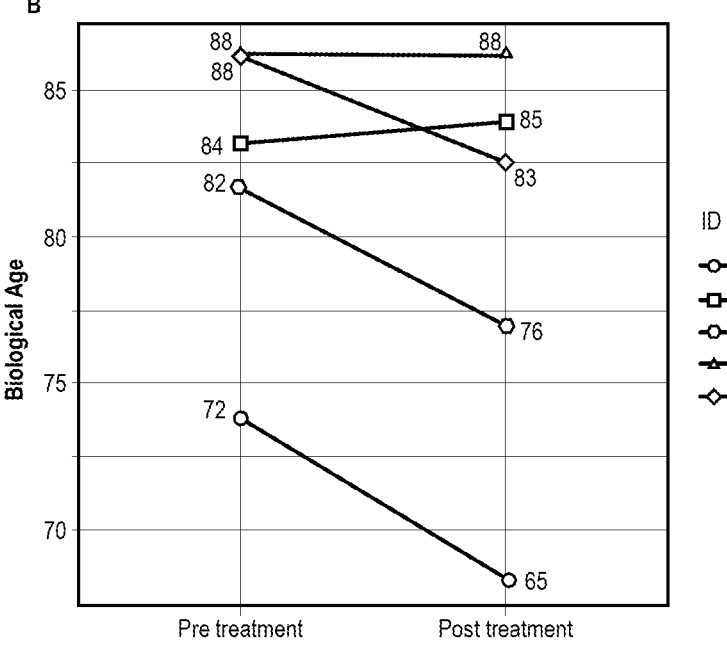
Figure 2C:
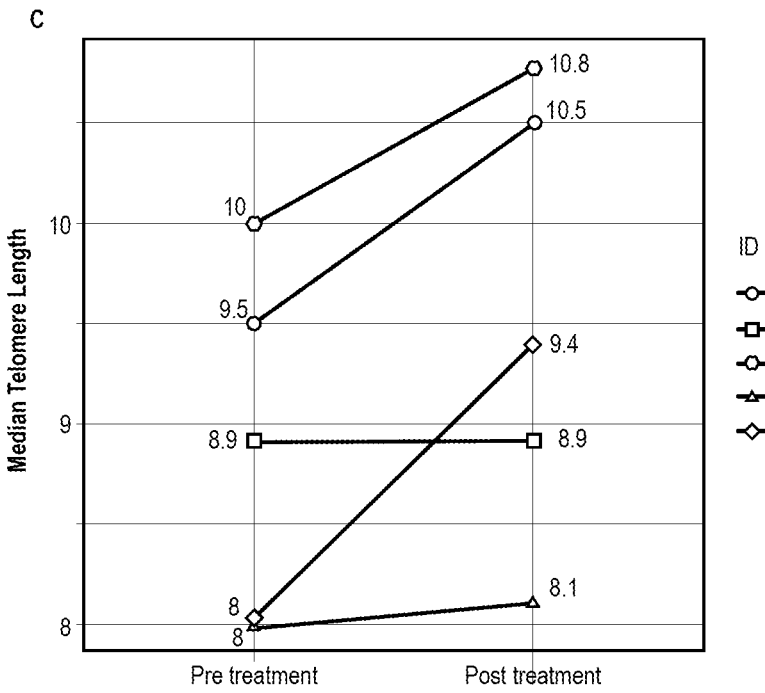
Figure 2D:
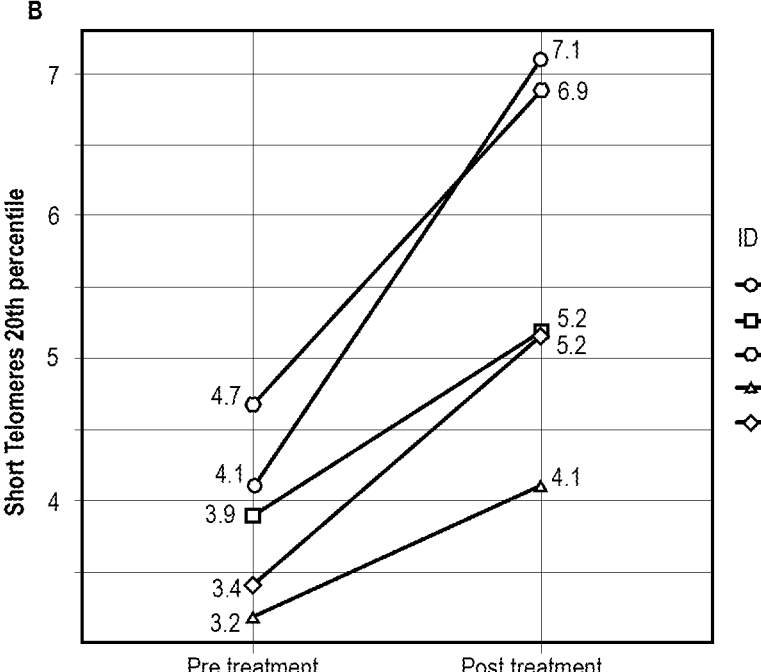

FIGS. 2A-2D demonstrate the test subjects' ages and telomere lengths pre-treatment and post-treatment. The pretreatment mean chronological age was 80.6 (SD=7.0) years and the post-treatment mean chronological age was 81.5 (SD=7.0) (FIG. 2A). The "biological age" (according to telomere length) decreased in four of the five patients with the pretreatment mean biological age measuring 82.8 years (SD=6.6) and the post treatment mean biological age measuring 79.4 years (SD=9.1) (FIG. 2B). There was an increase in the median telomere length in four of the five patients with the median pre-treatment telomere length being 8.88 (SD=0.89) and the median post treatment telomere length being 9.54 (SD=1.11) (FIG. 2C). There was an increased telomere length in the 20th percentile group of telomers in all 5 patients with the mean pretreatment measuring 3.86 (SD=0.59) and the mean post treatment measuring 5.70 (SD=1.27) (FIG. 2D). This increase was statistically significant (Wilcoxon Rank Sum test, P=0.027).

What is claimed is:

1. A method for treating age-related cognitive decline in a human, the method comprising:
   intranasally administering a therapeutically effective amount of a first recombinant viral vector, a second recombinant viral vector, and a third recombinant viral vector, each at a dose of at least $2 \times 10^{13}$ GC, to a human subject in need thereof,
   wherein the first recombinant viral vector comprises (i) an adeno-associated virus (AAV) backbone of serotype AAV8 and (ii) the telomerase reverse transcriptase (hTERT) gene,
   wherein the second recombinant viral vector comprises (i) an AAV backbone of serotype AAV9 and (ii) the hTERT gene,
   wherein the third recombinant viral vector comprises an AAV backbone of serotype AAV9 and the human klotho (KL) gene, and
   wherein administering the therapeutically effective amount of the first, second, and third recombinant viral vectors increases cognitive function during the first 3.5 months following administration, prevents decline in cognitive function during the first 5 months following administration, or both, as measured by standardized cognitive test scores.

2. The method of claim 1, wherein the first recombinant viral vector, second recombinant viral vector, third recombinant viral vector, or any combination thereof are administered at a dose of up to about $1 \times 10^{15}$ GC.

3. The method of claim 1, wherein the age-related cognitive decline is associated with dementia.

4. The method of claim 3, wherein the dementia is associated with Alzheimer's disease.

5. The method of claim 1, wherein the first, second, and third recombinant viral vectors are administered via intranasal injection.

6. The method of claim 5, wherein hyaluronidase is administered to the nares prior to administration of the recombinant viral vectors.

7. The method of claim 1, further comprising administering an immunosuppressant concurrently with administration of the first, second, and third recombinant viral vectors, following administration of the first, second, and third recombinant viral vectors, or both.

8. The method of claim 1, wherein the method omits administering any human genes other than hTERT and KL.

9. The method of claim 1, wherein administering the therapeutically effective amount of the first, second, and third recombinant viral vectors comprises delivering a ratio of hTERT genes to KL genes of at least 1.5 up to a ratio of hTERT genes to KL genes of 2.5.

10. The method of claim 1, wherein administering the therapeutically effective amount of the first, second, and third recombinant viral vectors comprises delivering a ratio of hTERT genes to KL genes of at least 1.25 up to a ratio of hTERT genes to KL genes of 5.

11. A method for treating age-related cognitive decline in a human, the method comprising:

intranasally administering a therapeutically effective amount of a first recombinant viral vector, a second recombinant viral vector, and a third recombinant viral vector, each at a dose of at least $2 \times 10^{13}$ GC, to a human subject in need thereof, wherein the first recombinant viral vector comprises (i) an adeno-associated virus (AAV) backbone of serotype AAV8 and (ii) the telomerase reverse transcriptase (hTERT) gene, wherein the second recombinant viral vector comprises (i) an AAV backbone of serotype AAV9 and (ii) the hTERT gene, wherein the third recombinant viral vector comprises an AAV backbone of serotype AAV9 and the human klotho (KL) gene, wherein the method omits administering any human genes other than hTERT and KL, and wherein administering the therapeutically effective amount of the first, second, and third recombinant viral vectors increases cognitive function during the first 3.5 months following administration, prevents decline in cognitive function during the first 5 months following administration, or both, as measured by standardized cognitive test scores.

12. The method of claim 11, wherein the age-related cognitive decline is associated with dementia, Alzheimer's disease, or both.

13. The method of claim 11, wherein the first, second, and third recombinant viral vectors are administered by intranasal injection.

14. The method of claim 11, wherein hyaluronidase is administered to the nares prior to administration of the recombinant viral vectors.

15. The method of claim 11, further comprising administering an immunosuppressant concurrently with administration of the first, second, and third recombinant viral vectors, following administration of the first, second, and third recombinant viral vectors, or both.

16. The method of claim 11, wherein the first recombinant viral vector, second recombinant viral vector, third recombinant viral vector, or any combination thereof at a dose of up to about $1 \times 10^{15}$ GC.

\* \* \* \* \*